(12) United States Patent
Patel et al.

(10) Patent No.: US 10,874,158 B2
(45) Date of Patent: *Dec. 29, 2020

(54) METHOD AND APPARATUS FOR ATTACHING A LIGHT TO A HEAD-WORN DEVICE

(71) Applicant: Illinois Tool Works Inc., Glenview, IL (US)

(72) Inventors: Nishank Patel, Appleton, WI (US); Eric Sommers, Appleton, WI (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,281

(22) Filed: Sep. 9, 2019

(65) Prior Publication Data
US 2020/0000168 A1    Jan. 2, 2020

Related U.S. Application Data

(63) Continuation of application No. 15/334,838, filed on Oct. 26, 2016, now Pat. No. 10,405,597.

(51) Int. Cl.
| | |
|---|---|
| *A42B 3/04* | (2006.01) |
| *F21L 4/08* | (2006.01) |
| *F21V 33/00* | (2006.01) |
| *F21V 23/04* | (2006.01) |
| *F21V 21/088* | (2006.01) |
| *F21V 21/14* | (2006.01) |

(Continued)

(52) U.S. Cl.
CPC .............. *A42B 3/0446* (2013.01); *A61F 9/06* (2013.01); *A61F 9/067* (2013.01); *F21L 4/085* (2013.01); *F21V 21/0885* (2013.01); *F21V 21/145* (2013.01); *F21V 23/0414* (2013.01); *F21V 23/0464* (2013.01); *F21V 33/0008* (2013.01); *A61F 9/022* (2013.01); *A61F 9/061* (2013.01); *F21W 2131/402* (2013.01)

(58) Field of Classification Search
CPC .......... A42B 3/0446; A61F 9/06; A61F 9/067; A61F 9/022; A61F 9/061; F21L 4/085; F21V 21/0885; F21V 21/145; F21V 23/0414; F21V 23/0464; F21V 33/0008; F21W 2131/402
USPC ....................................................... 362/105
See application file for complete search history.

(56) References Cited

U.S. PATENT DOCUMENTS

| | | | |
|---|---|---|---|
| 3,440,662 A | 4/1969 | O'Shea | |
| 5,438,494 A * | 8/1995 | Harlan | A42B 1/244 24/3.9 |

(Continued)

FOREIGN PATENT DOCUMENTS

| | | |
|---|---|---|
| CN | 104930359 | 9/2015 |
| DE | 673452 | 3/1939 |

(Continued)

OTHER PUBLICATIONS

Int'l Search Report and Written Opinion for PCT/US217/058234 dated Jan. 25, 2018 (14 pgs).

*Primary Examiner* — Cara E Rakowski
*Assistant Examiner* — Jessica M Apenteng
(74) *Attorney, Agent, or Firm* — McAndrews, Held & Malloy, Ltd.

(57) ABSTRACT

Provided is a light attached to a helmet where the light does not move when a face shield of the helmet is rotated up or down.

20 Claims, 8 Drawing Sheets

(51) Int. Cl.
*A61F 9/06* (2006.01)
*F21W 131/402* (2006.01)
*A61F 9/02* (2006.01)

(56) References Cited

U.S. PATENT DOCUMENTS

| | | | |
|---|---|---|---|
| 6,616,294 B1 | | 9/2003 | Henry |
| 8,381,318 B2 * | | 2/2013 | Junker .................. A42B 3/044 |
| | | | 2/422 |
| 9,010,955 B2 * | | 4/2015 | Robinson .............. F21V 21/084 |
| | | | 362/105 |
| 2011/0107491 A1 | | 5/2011 | Sanders |

FOREIGN PATENT DOCUMENTS

| | | |
|---|---|---|
| EP | 0917865 | 5/1999 |
| FR | 2438229 | 4/1980 |

\* cited by examiner

METHOD AND APPARATUS FOR ATTACHING A LIGHT TO A HEAD-WORN DEVICE

CLAIM OF PRIORITY/INCORPORATION BY REFERENCE

This patent application is a continuation of U.S. patent application Ser. No. 15/334,838 filed on Oct. 26, 2016, which is hereby incorporated herein by reference in its entirety.

BACKGROUND

The present disclosure relates to lighting a work area, and more particularly, to a method and apparatus for attaching a light to a head-worn device.

Some work environments, such as, for example, a welding environment, can be dark and in some cases confined. Accordingly, in such cases lighting can be difficult to focus on the specific spot that is in need of illumination for the operator to clearly view through, for example, their welding helmet. Due to the confined spaces and the need to maneuver around work pieces, a light attachment needs to be solidly mounted to the protective device so it does not become dislodged or out of adjustment if bumped against items within the weld environment.

Limitations and disadvantages of conventional systems for lighting a work area will become apparent to one of skill in the art through comparison of such approaches with some aspects of the present method and system set forth in the remainder of this disclosure with reference to the drawings.

SUMMARY

Methods and systems are provided for a method and apparatus for lighting a work area, substantially as illustrated by and described in connection with at least one of the figures, as set forth more completely in the claims.

BRIEF DESCRIPTION OF THE DRAWINGS

These and/or other aspects will become apparent and more readily appreciated from the following description of some example embodiments, taken in conjunction with the accompanying drawings.

DETAILED DESCRIPTION

Various embodiments of the disclosure are described that provide secure anchoring without altering the welding helmet. Accordingly, since the various embodiments do not alter the helmet structures and hence comply with original testing configurations, certifications such as ANSI, CSA, CE, etc. can still be valid.

An embodiment of the disclosure is a light mounting device comprising an anchor bezel configured to couple to a head-worn device that has a protective shield that can be rotated up or down and a constant-angle portion. The head-worn device also comprise a bezel rotational lock configured to maintain the anchor bezel at a substantially constant angle relative to the constant-angle portion when the protective shield is rotated and a light source connector configured to adjustably couple a light source holder to the anchor bezel, where the light source connector enables changing an angle of the light source holder with respect to the constant-angle portion. The light source holder is configured to hold a light source, where the anchor bezel is configured to attach to the head-worn device such that when the protective shield is rotated with respect to the constant-angle portion, the angle of the light source with respect to the constant-angle portion is held substantially constant. The light source holder comprises a clip to enable attachment and detachment of the light source from the light source holder.

A light bracket arm is configured to couple to the anchor bezel at one portion of the light bracket arm and to the light source connector at another portion of the light bracket arm. Various embodiments may have the light bracket arm be flexible such that the light bracket arm can be bent to a desired shape. Furthermore, at least one of the light source holder, the light source connector, and the light bracket arm can be detachable to enable attachment and detachment of the light source from the head-worn device.

The anchor bezel can comprise at least one of a washer, a bushing, or a pivot tensioning knob, where the washer, the bushing, or the pivot tensioning knob is configured to be attached to the head-worn device.

The anchor bezel is configured to attach at a side of the head-worn device, and the anchor bezel, the light source connector, and the light source holder are configured to orient the light source toward a front of the head-worn device. The anchor bezel is connected to the head-worn device substantially near a pivot point of the protective shield.

In some embodiments of the disclosure, the light source holder is connected by a retractable cord to the anchor bezel. The light source connector may be connected to the anchor bezel. In various embodiments, the light source is configured to turn off when the protective shield is raised and turn on when the protective shield is lowered. The light mounting device may also comprise a light sensor, wherein when ambient light sensed by the light sensor senses is above a threshold the light source is configured to turn off, and when the ambient light sensed by the light sensor is equal to or below the threshold the light source is configured to turn on.

Another embodiment of the disclosure is a head mounted device that comprises a support unit to support the head mounted device on a head of a wearer, a face shield rotatably mounted on a pivot point of the head mounted device, a light source holder configured to hold a light source, and a light mounting bracket coupled to the head mounted device at substantially the pivot point and configured to hold the light source at a constant angle relative to the support unit when the face shield is rotated with respect to the support unit.

Another embodiment of the disclosure is a welding helmet that comprises a support unit to support the welding helmet on a head of a wearer, a rotatable face shield, a shield mounting assembly comprising a fixed component that is fixed with respect to the support unit and a rotatable component that is rotatable with respect to the support unit to enable rotation of the face shield with respect to the support unit, a light source, and a light mounting bracket coupled to the fixed component of the shield mounting assembly and configured to hold the light source at a constant angle relative to the support unit when the face shield is rotated with respect to the support unit.

The light mounting bracket comprises an anchor bezel configured to couple the light mounting bracket to the shield mounting assembly, a bezel rotational lock configured to maintain the anchor bezel at the constant angle relative to the support unit, a light bracket arm to couple a bracket pivot to the anchor bezel, wherein the bracket pivot enables adjustment of an angle of the light source with respect to at least one of the support unit or the anchor bezel, and a light source holder to hold the light source, wherein the light source holder is adjustably coupled to the light bracket arm. The light source holder comprises a clip to enable attachment and detachment of the light source from the light source holder. In some embodiments, the light source holder is connected by a retractable cord to at least one of the light bracket arm, the bracket pivot, or the anchor bezel.

The light mounting bracket comprises at least one of a washer, a bushing, or a pivot tensioning knob. The light mounting bracket may detachably hold the light source. The light mounting bracket may comprise an anchor bezel to couple the light mounting bracket to the shield mounting assembly, a bracket pivot coupled to the anchor bezel to enable adjustment of an angle of the light source with respect to at least one of the support unit or the anchor bezel, and a light source holder to hold the light source.

The light mounting bracket may also comprise an anchor bezel to couple the light mounting bracket to the shield mounting assembly and to enable adjustment of an angle of the light source with respect to at least one of the support unit or the anchor bezel, a bezel rotational lock to selectively maintain the light source at the angle relative to the support unit, a light source holder to hold the light source, and a light bracket arm to couple the light source holder to the anchor bezel. The light source may be configured to turn off when the face shield is raised and turn on when the face shield is lowered.

Various embodiments may comprise a light sensor, where when ambient light sensed by the light sensor is above a threshold the light source is configured to turn off, and when the ambient light sensed by the light sensor is equal to or below the threshold the light source is configured to turn on.

Figure 1A:
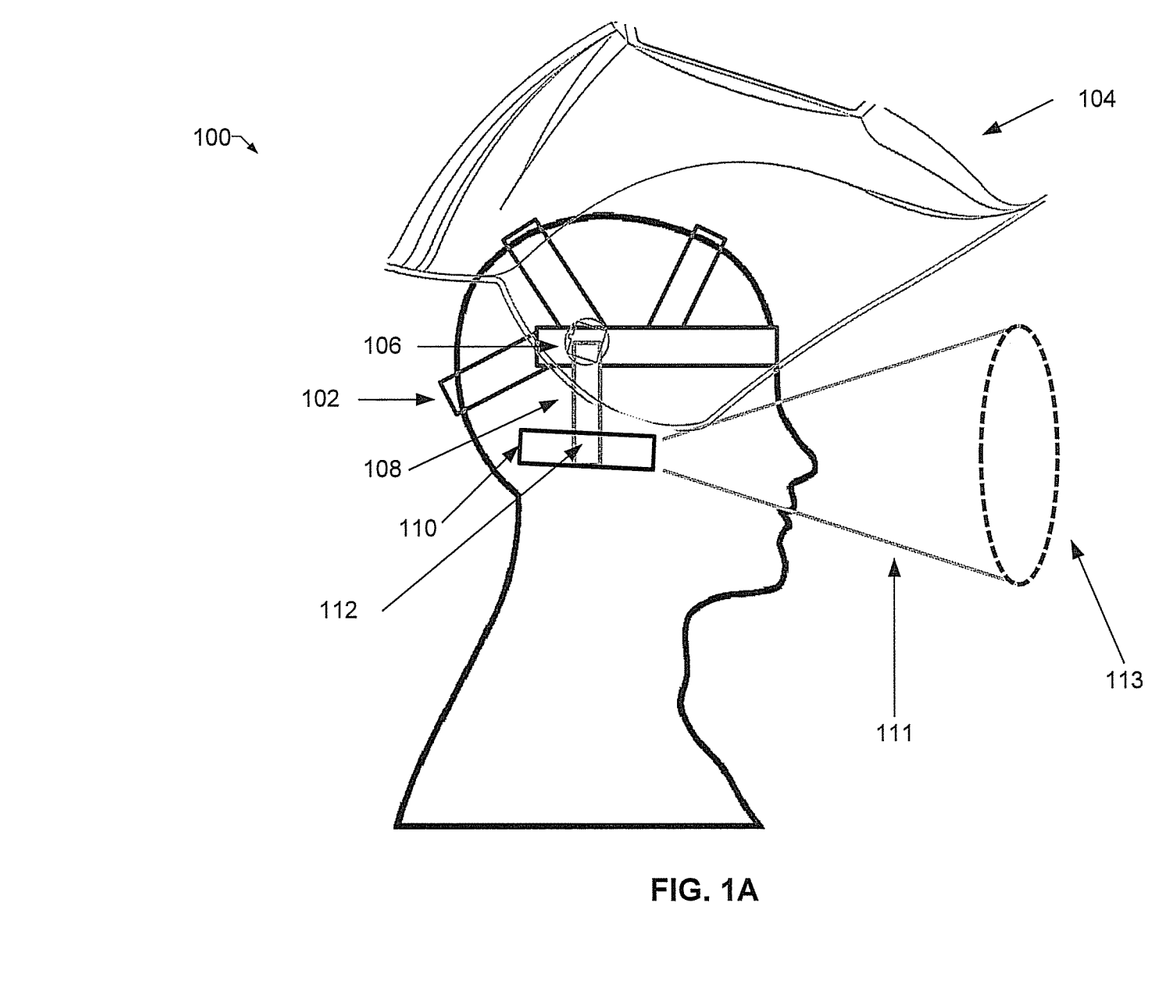
FIG. 1A is a drawing of an example helmet where the protective visor is not in use, in accordance with an embodiment of the disclosure.

FIG. 1A is a drawing of an example helmet where the protective visor is not in use, in accordance with an embodiment of the disclosure. Referring to FIG. 1A, there is shown a head-worn device 100 being worn by a user. The head-worn device 100 comprises a support unit 102 for wearing the head-worn device 100 on the head of the user, a protective shield 104 that is rotated up, an anchor (pivot) point 106 about which the protective shield 104 rotates up or down, a light bracket arm 108, and a light source 110. The light source 110 can be attached to the light bracket arm 108 via, for example, a light source holder 112. The light source holder 112 may be a separate piece from the light bracket arm 108 in some embodiments, and a single unit piece in other embodiments. The light source holder 112 may be any type of device that can hold a light source 110 such as, for example, a clip. When the light source 110 is turned on, the light beam 111 can shine on the work area 113.

The head-worn device 100 may be, for example, a welding helmet and the protective shield 104 may protect the user from the light of the welding torch as well as splattering material from the work area 113. Various embodiments of the disclosure have the light bracket arm 108 such that the light bracket arm 108 does not move substantially when the protective shield 104 is rotated up or down. This will be described in more detail below with FIGS. 2-6.

While in some cases, having additional lighting may still be helpful even when the protective shield 104 is rotated up, in other cases when the additional light is not needed, the light source 110 may be turned off to conserve power when the protective shield 104 is rotated up. Accordingly, in some embodiments the light source 110 can be provided with an on/off switch (not shown). Various embodiments may also provide for turning the light source 110 on/off depending on the position of the protective shield 104. For example, if the protective shield 104 is rotated up, the light source 110 may be turned off automatically, and if the protective shield 104 is rotated down, the light source 110 may be turned on automatically. The light source 110 may also be turned on or off automatically depending on the ambient light sensed by a sensor (not shown) on the head-worn device 100.

A user interface (not shown) may facilitate controlling the light source 110. The user interface may comprise an on/off switch, a switch to allow automatically turning on and off the light source 110, whether by movement of the protective shield 104 or by a light sensor (not shown). The user interface may control the light source 110 via a wireless connection or a wired connection. The light sensor may communicate with the user interface via a wireless connection or a wired connection. The light sensor may be placed at any convenient place on the interior or exterior of the head-worn device 100, attached or hanging on the body of the user (on clothing, hanging around the neck, etc.), or placed in a nearby location.

The light source 110 shown is a basic representation of a light that could be used. Given current battery and LED light technology, lights can be much more efficient, but most welders need lighting throughout their shift, in many cases 8-10 hours. Due to this longevity requirement, some embodiments may provide a larger battery to eliminate the need to change batteries through the day. In various embodiments, the light source 110 could have replaceable batteries and/or an internal rechargeable battery.

Where the light does not need to be on for an extended period of time, but weight is an issue, the light source 110 may use smaller "coin" batteries. Still other embodiments may require very bright lights for a long period of time. In such cases, a battery pack (not shown) may be connected to the light source 110, where the battery pack may be attached to a different portion of the head-worn device 100, to a wearable item such as a work belt of the user, or worn on the body, for example, by strapping the battery on to the user's back. Still other embodiments may use a light source 110 that can receive power wirelessly. Accordingly, various embodiments of the disclosure are not limited to a specific type of light or power for the light.

Figure 1B:
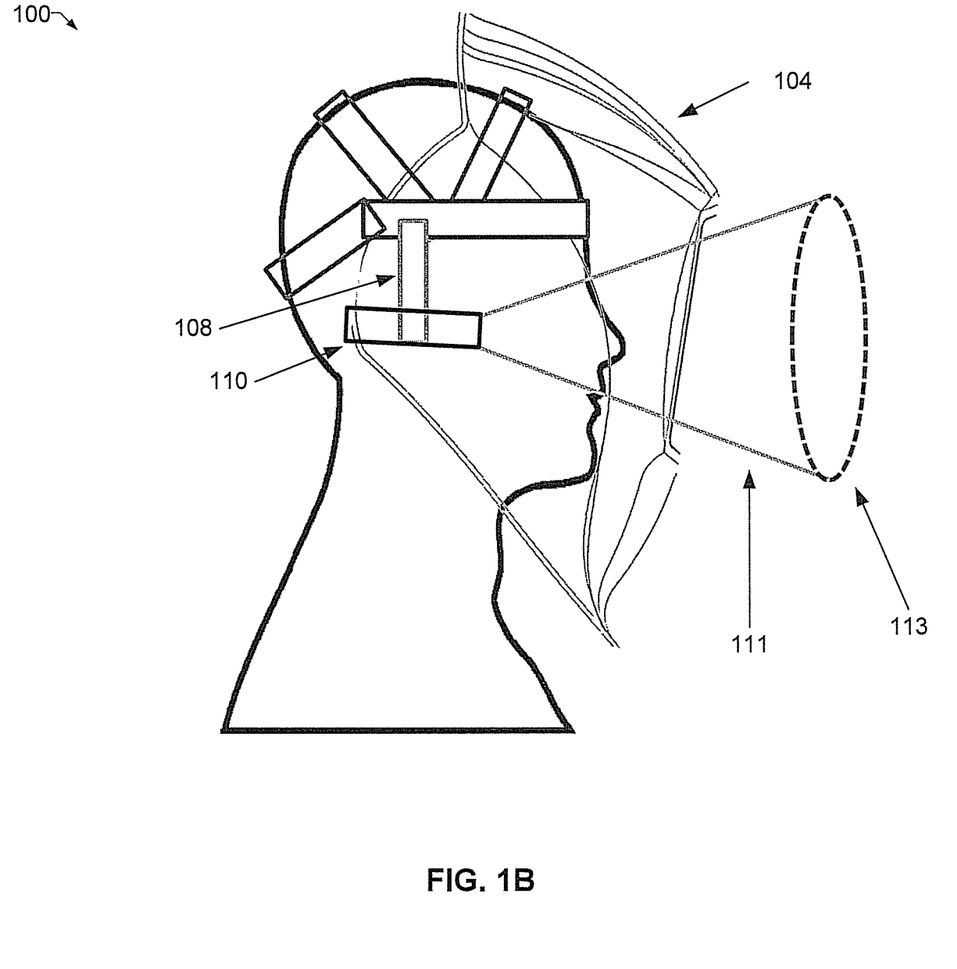
FIG. 1B is a drawing of an example helmet where the protective visor is in use, in accordance with an embodiment of the disclosure.

FIG. 1B is a drawing of an example helmet where the protective visor is in use, in accordance with an embodiment of the disclosure. Referring to FIG. 1B, there is shown the head-worn device 100 being worn by a user similarly as in FIG. 1A except that the protective shield 104 is rotated down to protect the user. Various embodiments of the disclosure will allow the light bracket arm 108, and hence the light source 110, to remain substantially stationary even when the protective shield 104 is rotated up or down.

Figure 2:
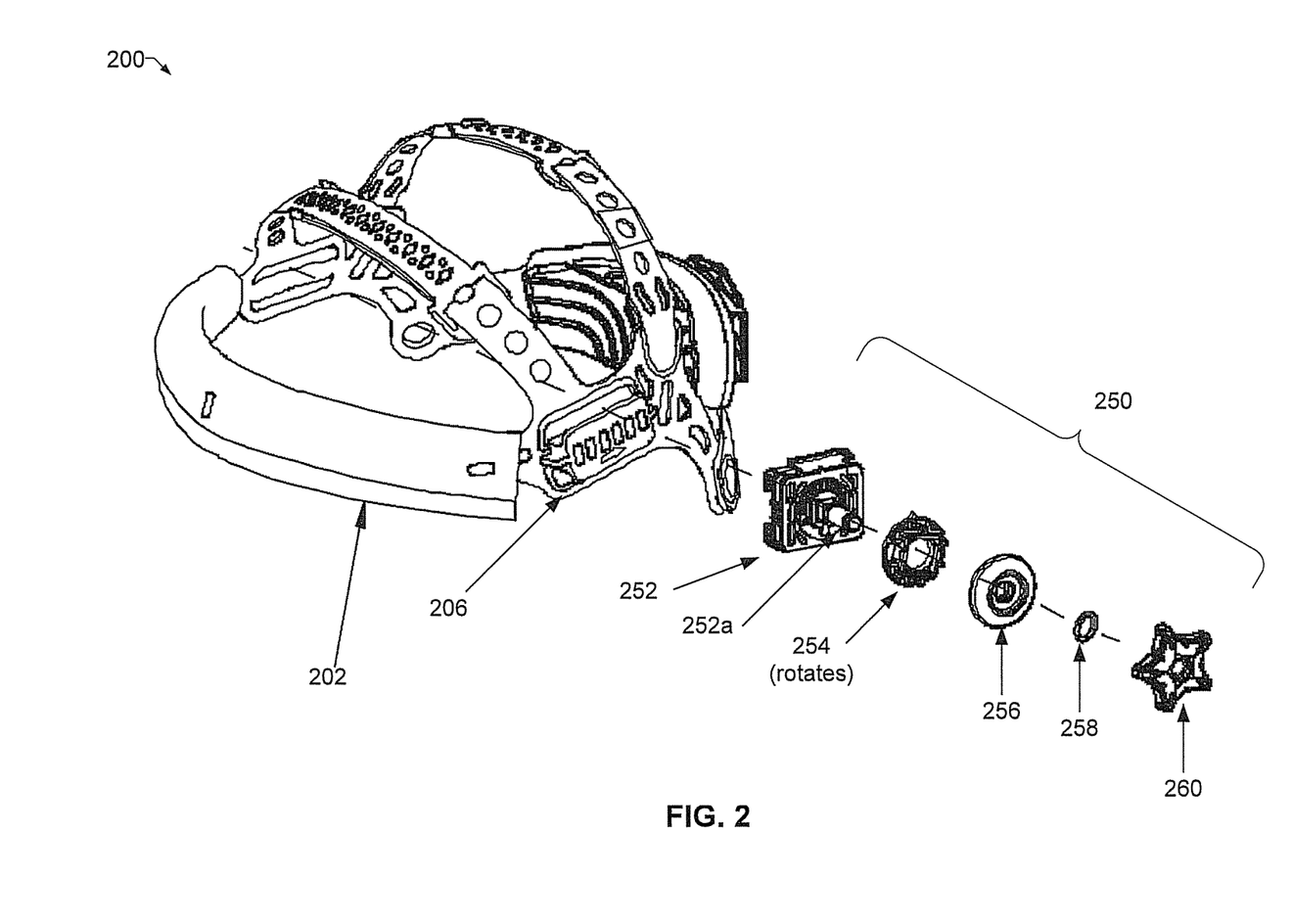
FIG. 2 is a drawing of an example device for attaching a light to a helmet, in accordance with an embodiment of the disclosure.

FIG. 2 is a drawing of an example device for attaching a light to a helmet, in accordance with an embodiment of the disclosure. Referring to FIG. 2, there is shown the head-worn device 200 comprising the support unit 202 that may be similar to the support unit 102. A light mounting assembly 250 is attached at the anchor (pivot) point 206, which is similar to the anchor (pivot) point 106 about which the protective shield 104 rotates. The light mounting assembly 250 can comprise a headband depth positioning slide 252 that is locked to the support unit 202. The rotating coupler 254 is rotatably attached to the headband depth positioning slide 252.

The rotating coupler 254 rotates with a protective shield such as, for example, the protective shield 104. Next to the rotating coupler 254 is the headgear washer 256, a headgear o-ring 258, and a pivot tensioning knob 260. The rotating coupler 254, the headgear washer 256, the headgear o-ring 258, and the pivot tensioning knob 260 can be mounted on, for example, an axle 252a protruding from the headband depth positioning slide 252. While the rotating coupler 254 can rotate about the axle 252a, the headgear washer 256, the headgear o-ring 258, and the pivot tensioning knob 260 do not rotate about the axle 252a once those components are tightened in place by the pivot tensioning knob 260. The pivot tensioning knob 260 may also be referred to as a constant-angle portion since it should not rotate when the protective shield 104 is rotated up or down. Other parts that also do not rotate with the protective shield 104, such as, for example, headgear washer 256 or the headgear o-ring 258, may also be referred generally as the constant-angle portion.

Accordingly, the light source 110 that can be attached to the headgear washer 256 via the light bracket arm 108 will not move by any substantial amount when the protective shield 104, which may be coupled to the rotating coupler 254, is rotated up or down. In various embodiments, the rotating coupler 254 and/or the protective shield 104 may be designed such that the protective shield 104 can stay in any position where it is placed. Other embodiments may have detents at specific positions so that the protective shield 104 can stay at any one of those locations. The present disclosure is not limited to the protective shield being in a specific location.

The headband depth positioning slide 252 may also be referred to as an anchor bezel, and the rotating coupler 254 as a bezel rotational lock.

Referring back to FIGS. 1A and 1B, the headgear washer 256 can be connected to the light bracket arm 108, while some embodiments may have the headgear washer 256 and the light bracket arm 108 as a single piece. The light bracket arm 108 can be configured to drop down the side of the user's head with the light source 110 attached to the lower end of the light bracket arm 108. The light source 110 may be attached to the light bracket arm 108 by any suitable means. For example, the lower end of the light bracket arm 108 may comprise a clip that a light source 110 can be inserted in to. For example, the clip may be spread apart when the light source 110 is pressed in to it, and then clamp tightly around the light source 110 when the light source 110 is in position.

Other types of attachments points could be, for example, ball and socket joint, magnet, a tube in to which the light source 110 is inserted, etc. The light source 110 may be attached to the light bracket arm 108 such that the light source 110 can be rotated to shine the light up or down. When a ball and socket joint is used to attach the light source 110 to the light bracket arm 108, the light source 110 may be moved side to side as well as up and down. Various embodiments of the disclosure may also use another joint to allow side to side movement for the light source 110. Accordingly, the light source 110 can be attached to the light bracket arm 108 via one of many types of light source holders. Furthermore, a flexible bracket can be used for the light bracket arm 108 to allow the light bracket arm 108 to be bent to a desired shape to allow the light source 110 to shine to the desired work area.

Accordingly, because the headgear washer 256 locks into the headband depth positioning slide 252 that is locked to the support unit 102 so that the light source 110 stays constantly positioned with respect to the user's head-worn device 200.

Figure 3:
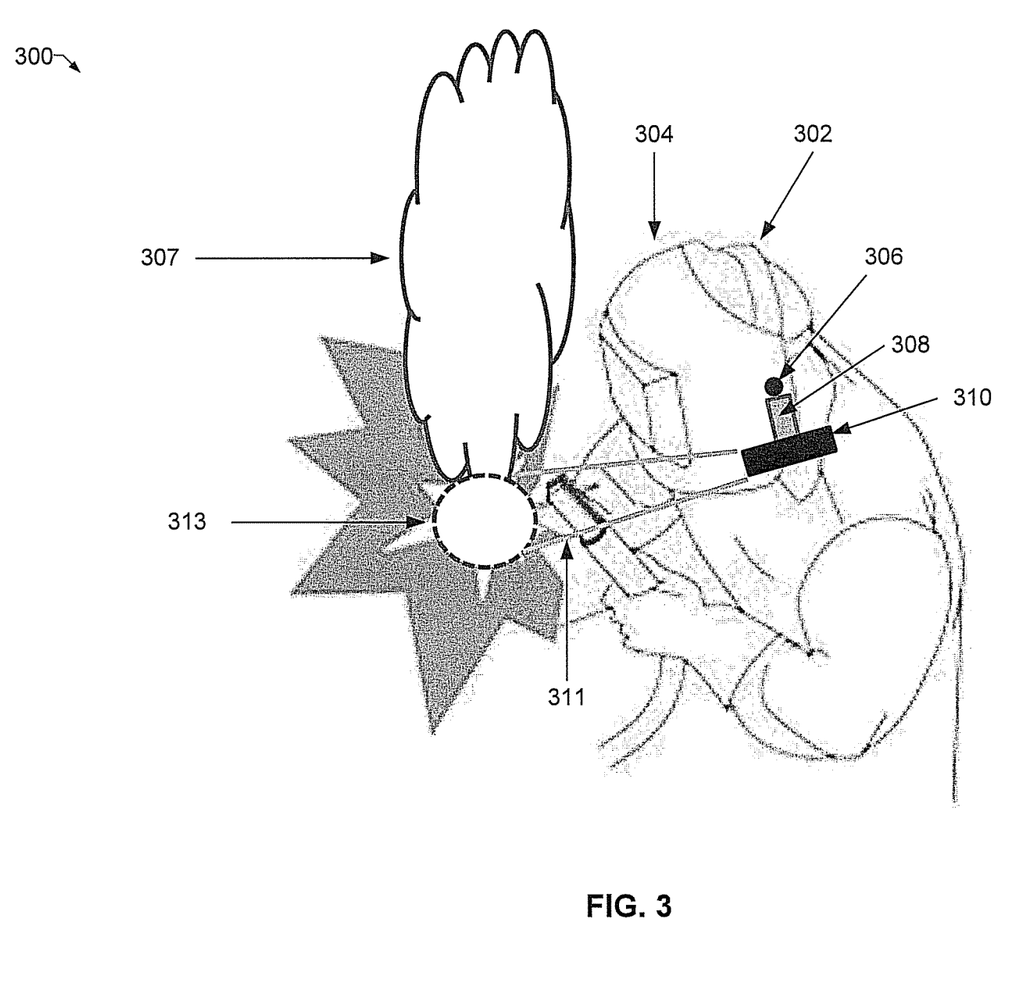
FIG. 3 is a drawing of an example of a light shining on a work area without shining into a weld plume, in accordance with an embodiment of the disclosure.

FIG. 3 is a drawing of an example of a light shining on a work area without shining into a weld plume, in accordance with an embodiment of the disclosure. Referring to FIG. 3, there is shown a welder wearing a welding helmet 300 that comprises the support unit 302 and the welding shield 304. The light source 310 is connected to the welding helmet 300 at the anchor (pivot) point 306 via the light bracket arm 308.

As the welder is welding the work area 313, there may be a weld plume 307 that rises from the work area 313. At times, depending on the amount and type of weld plume, light shining on the weld plume may obscure the vision of the welder. Accordingly, it may be desirable at times to avoid shining light on to a weld plume. This is illustrated in this figure where the light beam 311 shines on the work area 313 without shining in to the weld plume 307. Accordingly, the light beam 311 shines on the work area 313 without being dissipated or obscured by the weld plume 307, or illuminating the weld plume 307 to further obstruct vision of the welder.

Figure 4:
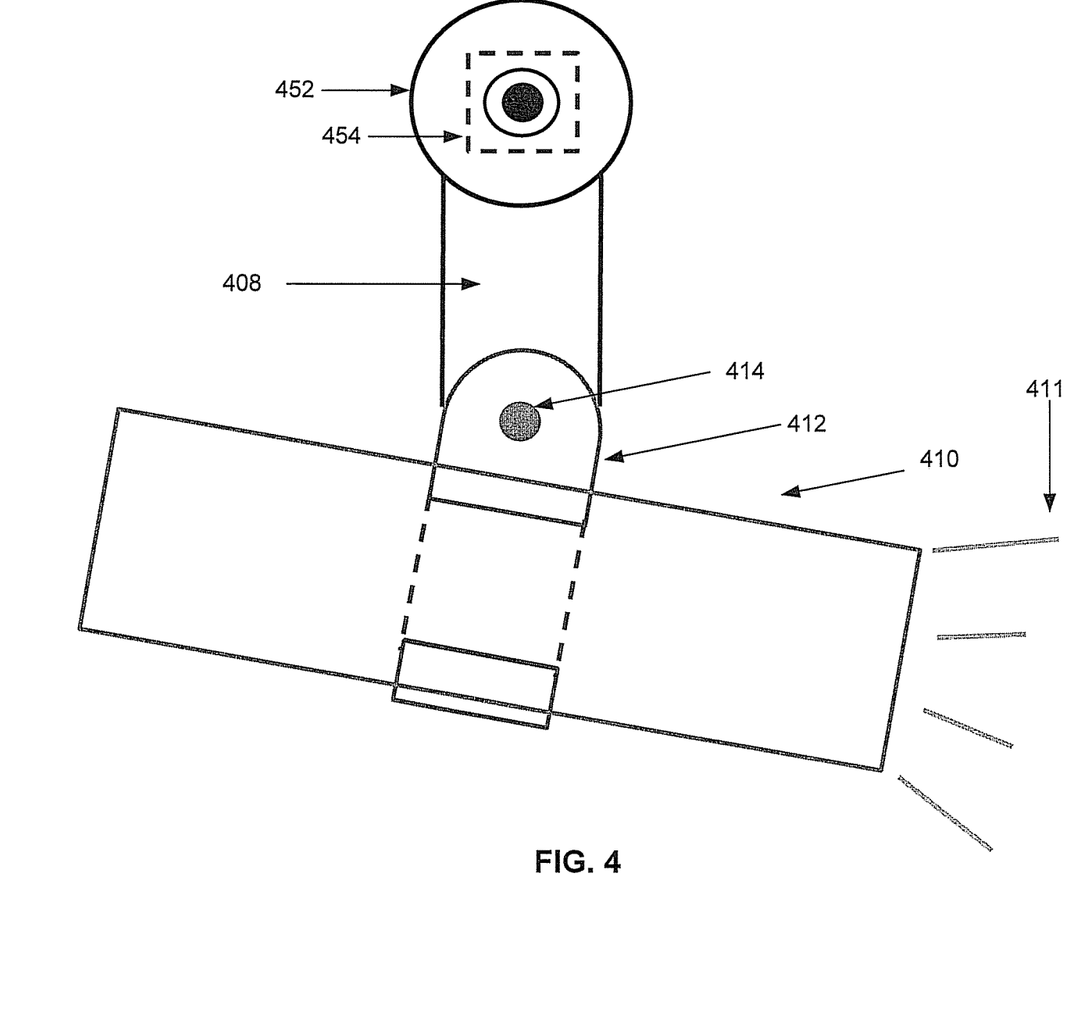
FIG. 4 is a drawing of an example light bracket arm for attaching a light to a helmet, in accordance with an embodiment of the disclosure.

FIG. 4 is a drawing of an example bracket for attaching a light to a helmet, in accordance with an embodiment of the disclosure. Referring to FIG. 4, there is shown the light bracket arm 408 connected to the anchor bezel 452, with the bezel rotational lock 454 on the underside of the anchor bezel 452. The light bracket arm 408 drops down from the anchor bezel 452 via a bezel rotational lock 454 that is shown in a simple rotational configuration. Other types of pivots could be used at this point, such as ball and socket, etc., to give the operator additional flexibility in positioning the light beam 411. The light source holder 412 is coupled to the light bracket arm 408, and securely holds the light source 410. The light source holder 412 may comprise a light source connector 414 for rotatably coupling the light source holder 412 to the light bracket arm 408.

For embodiments where the light source holder 412 is directly coupled to the anchor bezel 452, the light source connector 414 may rotatably couple the light source holder 412 to the anchor bezel 452.

Figure 6A:
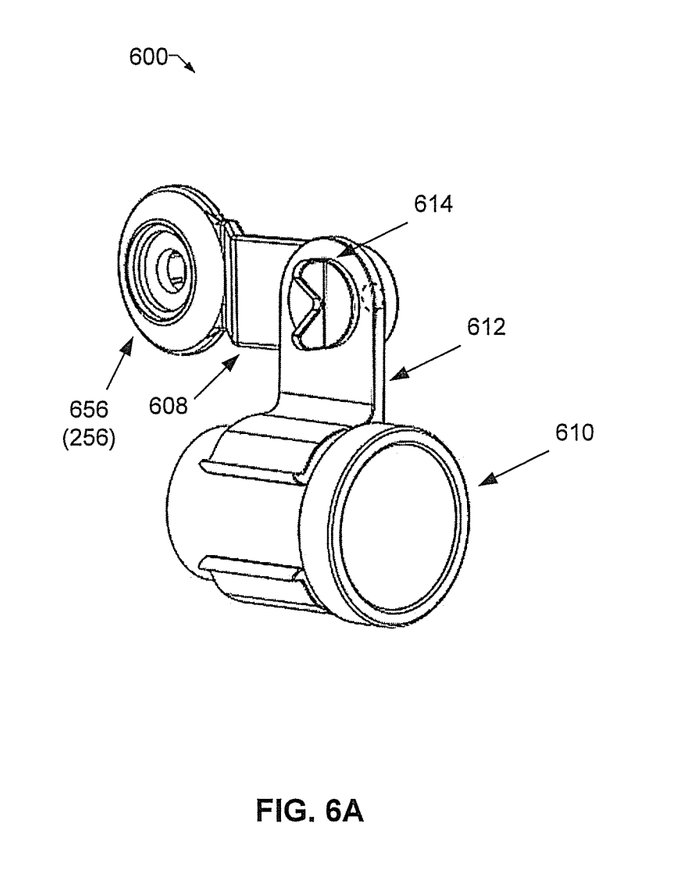
FIG. 6A is a drawing of an example light attachable to a head-worn device, in accordance with an embodiment of the disclosure.
Figure 6B:
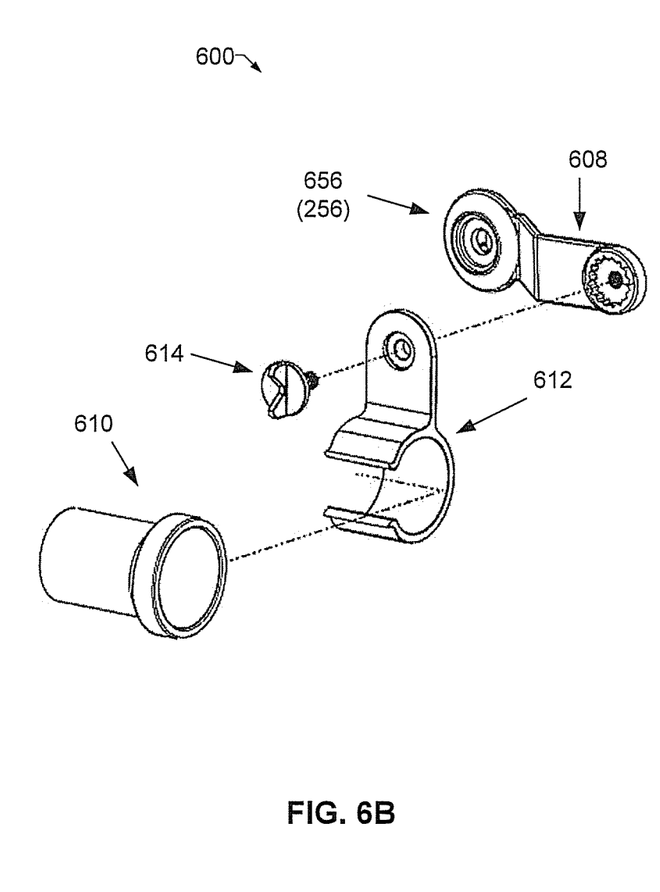
FIG. 6B is an exploded drawing of an example light attachable to a head-worn device, in accordance with an embodiment of the disclosure.

In various embodiments of the disclosure, the light bracket arm 408 drops down from the headgear anchor (pivot) point 106 (or 306) on a side of a head-worn device, thereby allowing the light source 410 to cast the light beam 411 on a work area (313) from below the weld plume (307). The light bracket arm 408 may also extend at different angles as shown in FIGS. 6A and 6B. Accordingly, various embodiments may have the light bracket arm 408 set at different angles or have the angle of the light bracket arm 408 be adjustable and allow it to be locked at different angles.

Various embodiments of the disclosure also allow the light, for example, the light source 410, to be separated from the light source holder 412 to allow the operator to easily remove and replace the light source 410 for use in other tasks around the work area. Other tasks could include, for example, inspecting welds or other items needing lighting where a head-worn device 100 might not allow access. The light source 410 may be further attached to the light source holder 412 by a retractable cord to allow the light source 410 to be returned more surely. Other embodiments may allow the light source holder 412, with the light source 410, to be removed from the light bracket arm 408. Some of these embodiments may also have a retractable cord to allow the light source holder 412 to be re-connected to the light bracket arm 408 more surely.

Various embodiments may configure the light source 410 to connect directly, for example, to the light bracket arm 408 with a type of corresponding attachment. For example, the light bracket arm 408 could have a receiving pin or hole that a corresponding hole or pin of the light source 410 would snap into, with detents molded into the faces of the flashlight or light bracket arm 408 to use for holding the desired angle of the light source 410.

An advantage of having the light bracket arm 408 directly connected at the headgear anchor (pivot) point 106 or 306 is that since the light bracket arm 408 and the light source 410 lowers the center of gravity for weight borne by the welder, the weight transferred to the user's neck muscles is reduced.

Figure 5:
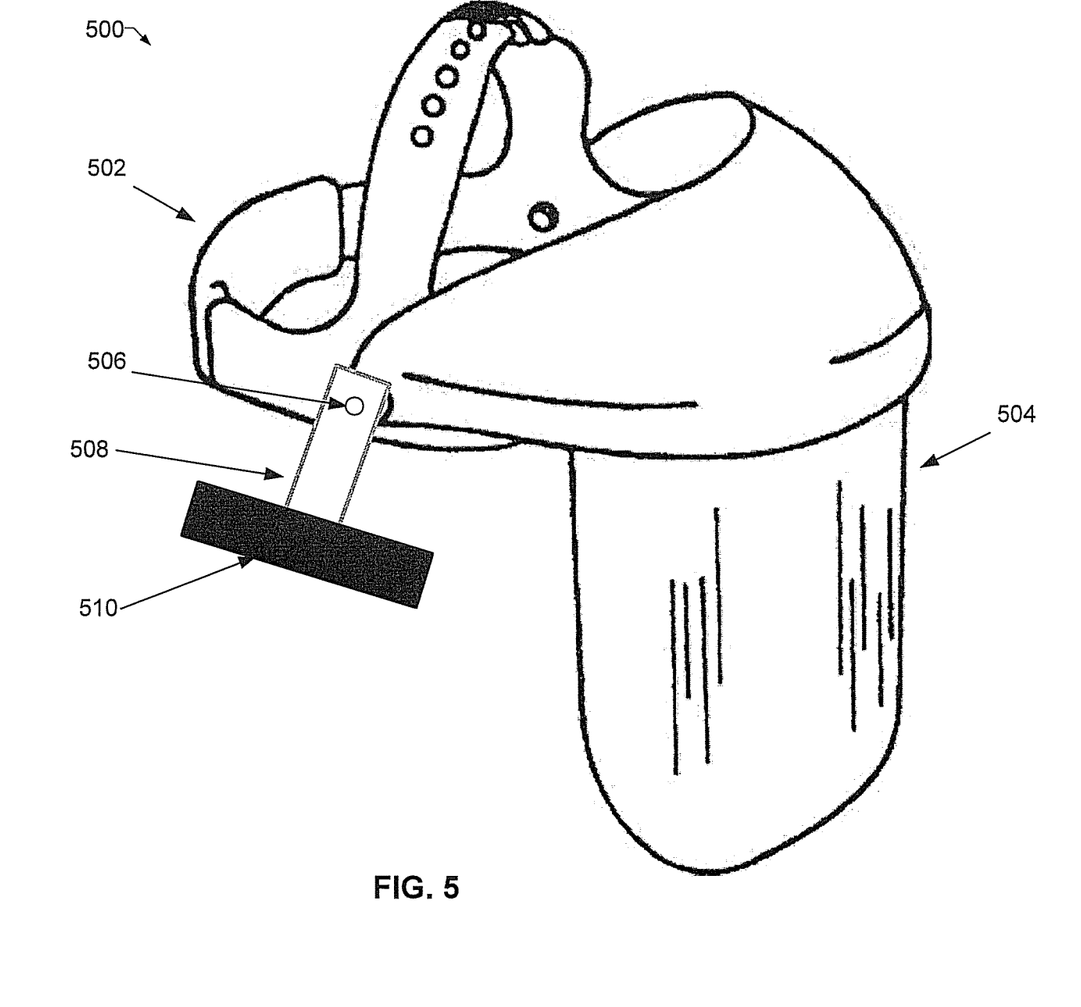
FIG. 5 is a drawing of an example helmet with an attached light, in accordance with an embodiment of the disclosure.

FIG. 5 is a drawing of an example helmet with an attached light, in accordance with an embodiment of the disclosure. Referring to FIG. 5, there is shown a grinding helmet 500 with a supporting unit 502, a protective shield 504, a light bracket arm 508 connected to the grinding helmet 500 at the anchor (pivot) point 506, and a light source 510. Similarly as described for other embodiments, the light source 510 does not substantially move when the protective shield 504 is rotated up or down.

FIG. 6A is a drawing of an example light attachable to a head-worn device, in accordance with an embodiment of the disclosure. Referring to FIG. 6A, there is shown a light unit 600 that can be attached to a head-worn device such as, for example, a welding helmet, a grinding helmet, etc. Other head-worn devices may be, for example, a fireman's helmet, a caver's helmet, climbing helmet, bicycle helmet, motorcycle helmet, safety helmet, etc.

The attachable light unit 600 comprises the light bracket arm 608 directly connected to the headgear washer 656, which corresponds to the headgear washer 256 of FIG. 2. The light source connector 614 fastens the light bracket arm 608 to the light source holder 612, which holds the light source 610.

FIG. 6B is an exploded drawing of an example light attachable to a head-worn device, in accordance with an embodiment of the disclosure. Referring to FIG. 6B, the exploded view shows the relationships of the various parts of the attachable light unit 600.

Figure 7:
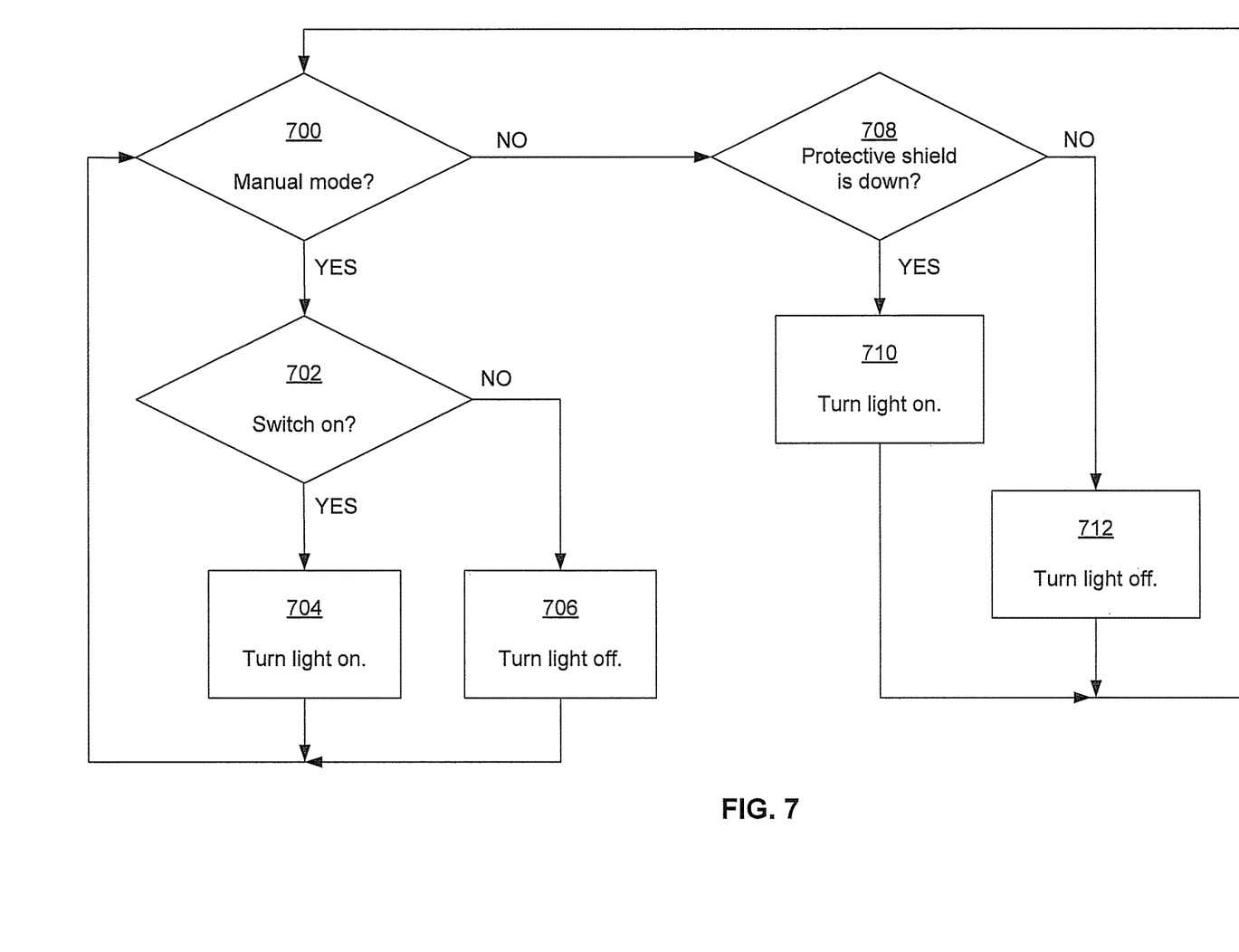
FIG. 7 is an example flow chart for controlling a light source, in accordance with an embodiment of the disclosure.

FIG. 7 is an example flow chart for controlling a light source, in accordance with an embodiment of the disclosure. Referring to FIG. 7, at 700 it is determined whether the light source control is in a manual mode. If it is in a manual mode, then at 702 it is determined whether the light switch is in the ON position. If so, the light source 110 is turned on at 704. Otherwise, the light source 110 is turned off (or stays off) at 706. From either 704 or 706, the process may proceed to 700.

If it is determined at 700 that the light source control is not in manual mode, then at 708 it is determined whether the protective shield 104 is in a down position. If so, then the light source 110 is turned on at 710. Otherwise the light source 110 is turned off (or stays off) at 712. The process may then continue back 700.

Proceeding from 704 or 706 may depend on, for example, an input such as the light switch and/or the manual/automatic mode being switched. Similarly, proceeding from 710 or 712 to 700 may depend on, for example, detection of movement in the protective shield and/or the manual/automatic mode being switched. Accordingly, it can be seen that there are many different ways to control the light, and various embodiments of the disclosure are not limited to any specific process.

Furthermore, this is just one process for determining whether to turn on or off the light source 110. Other embodiments may determine whether to turn on or off the light source 110 due to one or more light sensors detecting ambient light. Still other embodiments may incorporate both the light sensor and the protective shield position to determine whether to turn the light source on.

Other embodiments of the disclosure may have a head-worn device with a protective shield where the light bracket arm is rigidly mounted to the protective shield so that it moves up as the protective shield is rotated up. However, the light source holder may be configured to swivel to keep the light source shining on substantially the same work area. This may be accomplished, for example, with the light source and/or the light source holder weighted or balanced properly to maintain the lighting angle when it moves up or down with the rotation of the protective shield.

Various embodiments have disclosed a protective shield, and there are many types of protective shields that are encompassed by the disclosure. The present disclosure is not limited to any specific type of shield. For example, many protective shields may be a single piece that covers all or part of a face. Some protective shields, such as, for example, welding shields, may comprise a protective shield that can be rotated up and a visor that can be rotated up independently of the protective shield. In such cases of multiple parts that can be rotated up, various embodiments may generally refer to the protective shield as the largest unit that encompasses the multiple parts. However, the present disclosure need not be so limited. For example, for some embodiments, the visor that can be rotated up may also be referred to as a protective shield for the purposes of this disclosure.

As utilized herein, "and/or" means any one or more of the items in the list joined by "and/or." As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g." and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed:

1. A light mounting device, comprising:
   an anchor bezel configured to couple to a head-worn device that has a protective shield that can be rotated up or down and a constant-angle portion;
   a bezel rotational lock configured to maintain the anchor bezel at a substantially constant angle relative to the constant-angle portion when the protective shield is rotated;
   a light bracket arm, comprising an upper portion and a lower portion, coupled to the anchor bezel at the upper portion; and
   a light source holder, configured to hold a light source, coupled by a light source connector to the lower portion,
   wherein the anchor bezel is configured to attach to the head-worn device such that when the protective shield is rotated with respect to the constant-angle portion, an angle of the light source holder with respect to the constant-angle portion is held substantially constant.

2. The light mounting device of claim 1, wherein the light source connector is configured to adjustably couple the light source holder to the lower portion to enable changing the angle of the light source holder with respect to the constant-angle portion.

3. The light mounting device of claim 1, wherein the light source holder and the light bracket arm are a single unit piece.

4. The light mounting device of claim 1, wherein the light bracket arm is flexible such that the light bracket arm can be bent to a desired shape.

5. The light mounting device of claim 1, wherein at least one of the light source holder, the light source connector, or the light bracket arm is detachable to enable attachment and detachment of the light source from the head-worn device.

6. The light mounting device of claim 1, wherein at least one of the light source holder or the light source connector is detachable to enable attachment and detachment of the light source from the head-worn device.

7. The light mounting device of claim 1, wherein the anchor bezel comprises at least one of a washer, a bushing, or a pivot tensioning knob, the at least one of the washer, the bushing, or the pivot tensioning knob configured to be attached to the head-worn device.

8. The light mounting device of claim 1, wherein the anchor bezel is configured to attach at a side of the head-worn device, and the anchor bezel, the light source connector, and the light source holder are configured to orient the light source toward a front of the head-worn device.

9. The light mounting device of claim 1, wherein the anchor bezel is coupled to the head-worn device substantially near a pivot point of the protective shield.

10. The light mounting device of claim 1, wherein the light bracket arm comprises a retractable cord.

11. The light mounting device of claim 1, wherein the light source is configured to turn off when the protective shield is raised and turn on when the protective shield is lowered.

12. The welding helmet of claim 1, further comprising a light sensor, wherein when ambient light sensed by the light sensor is above a threshold the light source is configured to turn off, and when the ambient light sensed by the light sensor is equal to or below the threshold the light source is configured to turn on.

13. The light mounting device of claim 1, wherein the light bracket arm is adjustably coupled to the anchor bezel.

14. A head mounted device, comprising:
   a support unit configured to support the head mounted device on a head of a wearer;
   a face shield rotatably mounted on a pivot point of the head mounted device;
   a light source holder configured to hold a light source; and
   a light bracket arm, comprising an upper portion and a lower portion, coupled at the upper portion to a light mounting bracket of the head mounted device at substantially the pivot point and coupled at the lower portion to the light source holder,
   wherein the light mounting bracket is configured to hold the light source holder at a constant angle relative to the support unit when the face shield is rotated with respect to the support unit.

15. A welding helmet, comprising:
   a support unit configured to support the welding helmet on a head of a wearer;
   a face shield configured to be rotatable;
   a shield mounting assembly comprising a fixed component that is fixed with respect to the support unit and a rotatable component that is rotatable with respect to the support unit to enable rotation of the face shield with respect to the support unit;
   a light source holder configured to hold a light source; and
   a light bracket arm, comprising an upper portion and a lower portion, coupled at the upper portion to a light mounting bracket that is coupled to the shield mounting assembly, and coupled at the lower portion to the light source holder,
   wherein the light mounting bracket is configured to hold the light source holder at a constant angle relative to the support unit when the face shield is rotated with respect to the support unit.

16. The welding helmet of claim 15, wherein the light mounting bracket comprises:
   an anchor bezel configured to couple the light mounting bracket to the shield mounting assembly; and
   a bezel rotational lock configured to maintain the anchor bezel at the constant angle relative to the support unit, wherein:
      the light source holder is adjustably coupled to the light bracket arm, and
      the light bracket arm is coupled to the anchor bezel via a bracket pivot that is configured to enable adjustment of an angle of the light source holder with respect to at least one of the support unit or the anchor bezel.

17. The welding helmet of claim 16, wherein the light source holder comprises a clip to enable attachment and detachment of the light source from the light source holder.

18. The welding helmet of claim 16, wherein the light bracket arm comprises a retractable cord configured to connect the light source holder to at least one of the bracket pivot or the anchor bezel.

19. The welding helmet of claim 15, wherein the light mounting bracket comprises at least one of a washer, a bushing, or a pivot tensioning knob.

20. The welding helmet of claim 15, wherein the light mounting bracket is detachably coupled to the light source holder.

* * * * *